US012653596B2

(12) United States Patent
Jeong et al.

(10) Patent No.: US 12,653,596 B2
(45) Date of Patent: Jun. 16, 2026

(54) ELECTRODE UNIT AND ELECTRODE DEVICE INCLUDING SAME

(71) Applicant: DEEPQURE INC., Seoul (KR)

(72) Inventors: Chang Wook Jeong, Seoul (KR); Du Jin Bach, Seongnam-si (KR); Seok Hyeon Jo, Namyangju-si (KR)

(73) Assignee: DEEPQURE INC., Seoul (KR)

( * ) Notice: Subject to any disclaimer, the term of this patent is extended or adjusted under 35 U.S.C. 154(b) by 263 days.

(21) Appl. No.: 18/568,192

(22) PCT Filed: Jun. 14, 2021

(86) PCT No.: PCT/KR2021/007422
§ 371 (c)(1),
(2) Date: Dec. 7, 2023

(87) PCT Pub. No.: WO2022/260203
PCT Pub. Date: Dec. 15, 2022

(65) Prior Publication Data
US 2024/0407821 A1 Dec. 12, 2024

(30) Foreign Application Priority Data

Jun. 8, 2021 (KR) ......................... 10-2021-0073977

(51) Int. Cl.
*A61B 18/14* (2006.01)
*A61B 18/00* (2006.01)

(52) U.S. Cl.
CPC .... *A61B 18/00* (2013.01); *A61B 2018/00172* (2013.01); *A61B 2018/00434* (2013.01); *A61B 2018/00791* (2013.01)

(58) Field of Classification Search
CPC ................ A61B 18/00; A61B 18/1482; A61B 2018/00172; A61B 2018/00404;
(Continued)

(56) References Cited

U.S. PATENT DOCUMENTS 5,095,905 A * 3/1992 Klepinski ............ A61N 1/0556
600/377
2004/0049181 A1 3/2004 Stewart et al.
(Continued)

FOREIGN PATENT DOCUMENTS

CN 104363842 A 2/2015
CN 106308922 A 1/2017
(Continued)

OTHER PUBLICATIONS

European Search Report received for EP Application No. 21945270.3 on Apr. 3, 2025, 10 pgs.
(Continued)

*Primary Examiner* — Michael F Peffley
(74) *Attorney, Agent, or Firm* — Merchant & Gould P.C.

(57) ABSTRACT

An electrode unit provided in an electrode device for nerve denervation or modulation in vivo and disposed to enclose a tube-shaped tissue in the body includes an electrode layer formed by sequentially extending a fastening portion, an extension portion and an electrode portion, and the electrode portion including an electrode on one side and configured to enclose the tube-shaped tissue; and a fixing layer stacked with the fastening portion, the extension portion and a part of the electrode portion of the electrode layer.

10 Claims, 8 Drawing Sheets

(58) Field of Classification Search
CPC .......... A61B 2018/00434; A61B 2018/00511;
A61B 2018/00577; A61B 2018/00791;
A61B 2018/1407; A61N 1/05; A61N
1/0556; A61N 1/36
See application file for complete search history.

(56) References Cited

U.S. PATENT DOCUMENTS

| | | | |
|---|---|---|---|
| 2004/0082948 A1 | 4/2004 | Stewart et al. | |
| 2004/0111139 A1* | 6/2004 | McCreery | A61N 1/0556 607/117 |
| 2010/0211076 A1* | 8/2010 | Germain | A61B 18/1492 606/84 |
| 2019/0133681 A1* | 5/2019 | Jeong | A61B 18/0206 |
| 2020/0000514 A1 | 1/2020 | Weadock | |
| 2021/0085382 A1 | 3/2021 | Jeong | |
| 2023/0157747 A1* | 5/2023 | Jeong | A61B 18/1492 606/41 |

FOREIGN PATENT DOCUMENTS

| | | | |
|---|---|---|---|
| CN | 112888393 A | 6/2021 |
| JP | 2003-500099 A | 1/2003 |
| JP | 2016538054 A | 12/2016 |
| KR | 10-2013-0103763 A | 9/2013 |
| KR | 10-2013-0108401 A | 10/2013 |
| KR | 10-2013-0117294 A | 10/2013 |
| KR | 10-2014-0103446 A | 8/2014 |
| KR | 10-2015-0101290 A | 9/2015 |
| KR | 10-2016-0088393 A | 7/2016 |
| KR | 10-2018-0023824 A | 3/2018 |
| KR | 10-2018-0094955 A | 8/2018 |
| KR | 10-1912960 B1 | 10/2018 |
| KR | 1020210027161 A | 3/2021 |
| KR | 10-2244131 B1 | 4/2021 |
| WO | 2000/71043 A | 11/2000 |

OTHER PUBLICATIONS

International Search Report of PCT/KR2021/007422 dated Mar. 3, 2022, 4 pages.
Office action issued in counterpart application in Japan 2023-574520 on Oct. 29, 2024; 3 pages.
Chinese Office Action received for CN Application No. 202180099186.9 on Mar. 24, 2026, 14pgs.

* cited by examiner

100

ELECTRODE UNIT AND ELECTRODE DEVICE INCLUDING SAME

CROSS-REFERENCE TO RELATED APPLICATIONS

This application is a 35 U.S.C. 371 National Phase Application from PCT/KR2021/007422 filed on Jun. 14, 2021, which claims priority to and the benefit of Korean Patent Application No. 10-2021-0073977 filed on Jun. 8, 2021 in the Korean Intellectual Property Office, the disclosures of which are incorporated herein by reference in their entirety.

TECHNICAL FIELD

The present disclosure relates to an electrode unit for nerve denervation or modulation in vivo and an electrode device including the same.

BACKGROUND

A denervation is a surgical procedure intended to control an abnormally overactive autonomic nervous system by damaging specific nerves. For example, a renal denervation can treat hypertension and heart diseases by damaging renal sympathetic nerves directed to the kidney, and a pulmonary denervation can treat lung diseases by damaging parasympathetic nerves directed to the lung.

Nerves usually enclose the outer walls of tubes, such as blood vessels, bronchial tubes, etc., and it may be necessary to enclose the outer walls of tubes to measure signals from the nerves or transmit electrical impulses or various energies to the nerves to damage or destroy the nerves. For example, when a surgical procedure is performed on the renal artery, the main renal artery which is a procedure target has a diameter of from 5 mm to 7 mm, and the accessory renal artery having a diameter of from 1 mm to 2 mm may also be a procedure target. Also, the artery with distributed nerves varies in size from person to person and has different sizes depending on the location.

When the surgical procedure is performed as described above, it is important to delicately locate a component including an electrode to be formed at the end of a catheter so as to enclose the outer wall of the artery. Specifically, in order to effectively denervate or modulate the nerves, the component needs to enclose the outer wall of the artery with distributed nerves in a circumferential direction. Also, it is necessary to reliably and rapidly enclose the artery with the component including the electrode. Also, it is necessary to suppress or minimize unnecessary energy transfer and contact in the body. Korean Patent Laid-open Publication No. 2013-0108401 (published on Oct. 2, 2013) is one of the prior art documents.

DISCLOSURE OF THE INVENTION

Problems to be Solved by the Invention

The present disclosure is conceived to provide an electrode device including an electrode unit to be in contact with a human body and an electrode guide coupled to the electrode unit in minimum contact with each other and configured to manipulate the electrode unit.

The problems to be solved by the present disclosure are not limited to the above-described problems. There may be other problems to be solved by the present disclosure.

Means for Solving the Problems

According to an aspect of the present disclosure, an electrode unit provided in an electrode device for nerve denervation or modulation in vivo and disposed to enclose a tube-shaped tissue in the body includes an electrode layer formed by sequentially extending a fastening portion, an extension portion and an electrode portion, and the electrode portion including an electrode on one side and configured to enclose the tube-shaped tissue; and a fixing layer stacked with the fastening portion, the extension portion and a part of the electrode portion of the electrode layer.

According to the present disclosure, the fixing layer includes a first fastening portion formed on one end to correspond to the fastening portion; a second fastening portion formed on the other end; and a connection portion connecting the first and second fastening portions. A boundary between the connection portion and the second fastening portion is formed to be bendable.

According to the present disclosure, the fixing layer is attached to the electrode layer, but at least a part of the electrode portion of the electrode layer is not attached to the fixing layer.

According to the present disclosure, the first fastening portion of the fixing layer is attached corresponding to the fastening portion of the electrode layer, and all of the connection portion of the fixing layer is attached to the extension portion of the electrode layer and a part of the electrode portion of the electrode layer.

According to the present disclosure, the first fastening portion of the fixing layer is attached corresponding to the fastening portion of the electrode layer, and a part of the connection portion of the fixing layer is attached to the entire extension portion of the electrode layer, but the other part of the connection portion of the fixing layer is not attached to the electrode portion of the electrode layer.

According to the present disclosure, the first fastening portion of the fixing layer is attached corresponding to the fastening portion of the electrode layer, a part of the connection portion of the fixing layer is attached to the extension portion of the electrode layer and a part of the electrode portion of the electrode layer, and the other part of the connection portion of the fixing layer is not attached to the electrode portion of the electrode layer.

According to the present disclosure, a sensor unit disposed on the electrode portion of the electrode layer and configured to detect a temperature.

According to another aspect of the present disclosure, an electrode device for nerve denervation or modulation in vivo includes the electrode unit; and an electrode guide deformed into a wound state to bring the electrode unit into contact with the tube-shaped tissue. The electrode guide includes a body portion which is spaced apart from the electrode unit to enclose the circumference of the tube in the wound state; and a coupling portion which is connected to the end of the body portion and to which a fastening portion of the electrode unit is fixed.

According to the present disclosure, the coupling portion includes a first clamping piece fixed to the body portion; and a second clamping piece coupled to the first clamping piece with the fastening portion of the electrode unit interposed therebetween.

According to the present disclosure, any one of the first clamping piece and the second clamping piece includes a protrusion protruding in one direction, the other one of the first clamping piece and the second clamping piece includes a fastening groove recessed corresponding to the protrusion, and the fastening portion of the electrode unit includes a through-hole through which the protrusion penetrates.

According to the present disclosure, the fastening portion of the electrode unit is inserted between the first clamping piece and the second clamping piece.

According to the present disclosure, the electrode guide further includes a joint wire which penetrates the body portion and is coupled to the second clamping piece to guide the body portion to be in the wound state. The second clamping piece includes a wire groove formed to allow insertion of an end of the joint wire; and a fixing plate configured to close a portion of the wire groove in order to suppress deviation of the end of the joint wire from the wire groove.

The above-described aspects are provided by way of illustration only and should not be construed as liming the present disclosure. Besides the above-described embodiments, there may be additional embodiments described in the accompanying drawings and the detailed description.

Effects of the Invention

According to any one of the above-described aspects of the present disclosure, an electrode guide and an electrode unit can be spaced apart from each other in most sections in a wound state. Therefore, in a state where the separation space between the electrode unit and the electrode guide is exposed to air, a surgical procedure can be performed and heat generated from the electrode unit can be easily dissipated through convective heat transfer.

Also, according to any one of the above-described aspects of the present disclosure, while a coupling (assembly) point between the electrode unit and the electrode guide is minimized, the electrode unit can be stably supported by a coupling portion of the electrode guide. Thus, durability and reliability can be secured. Further, the electrode unit and the electrode guide can be easily assembled with each other.

Furthermore, since the electrode guide deformed into the wound state by power and the electrode unit in close contact with a tube in the body are configured separately from each other, it is possible to suppress the effects of power transmission, for example, transmission of a vibration or force to the tube in the body.

DETAILED DESCRIPTION

Figure 1:
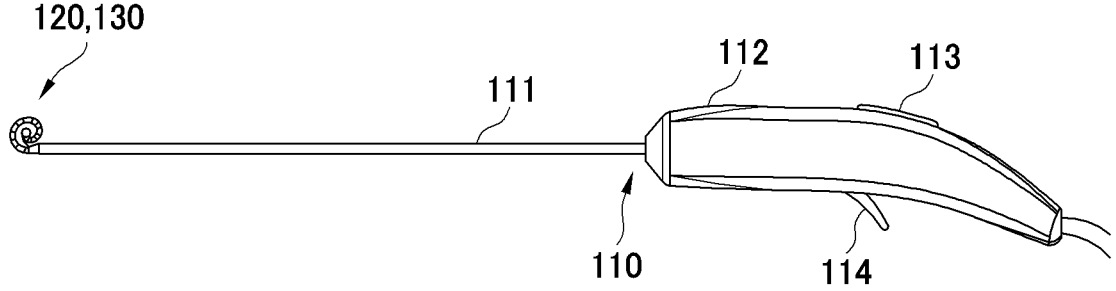
FIG. 1 is a side view of an electrode device according to an embodiment of the present disclosure.

Hereafter, example embodiments will be described in detail with reference to the accompanying drawings so that the present disclosure may be readily implemented by those skilled in the art. However, it is to be noted that the present disclosure is not limited to the example embodiments but can be embodied in various other ways. In the drawings, parts irrelevant to the description are omitted for the simplicity of explanation, and like reference numerals denote like parts through the whole document.

Through the whole document, a singular form expression includes a plural form expression unless it is clearly construed in a different way in the context.

In the embodiments disclosed in the present disclosure, well-known functions or constitutions will not be described in detail if they would unnecessarily obscure the embodiments of the present disclosure.

Through the whole document, it is to be understood that the term "comprises or includes" and/or "comprising or including" used in the document means that one or more other components, steps, operation and/or existence or addition of elements are not excluded in addition to the described components, steps, operation and/or elements unless context dictates otherwise and is not intended to preclude the possibility that one or more other features, numbers, steps, operations, components, parts, or combinations thereof may exist or may be added.

Through the whole document, the terms indicating positions or directions such as "up", "down", "left", "right", "front", "back" and the like are used to simply describe relative positions or directions of members with reference to the accompanying drawings, but do not limit the present disclosure.

The accompanying drawings are provided only to assist with an understanding of the embodiments of the present disclosure and are not intended to limit the technical conception of the present disclosure, and should be construed as covering all modifications, equivalents or alternatives that fall within the spirit and technical scope of the present disclosure.

Hereinafter, an exemplary embodiment of the present disclosure will be described in detail with reference to the accompanying configuration views or process flowcharts.

Figure 2:
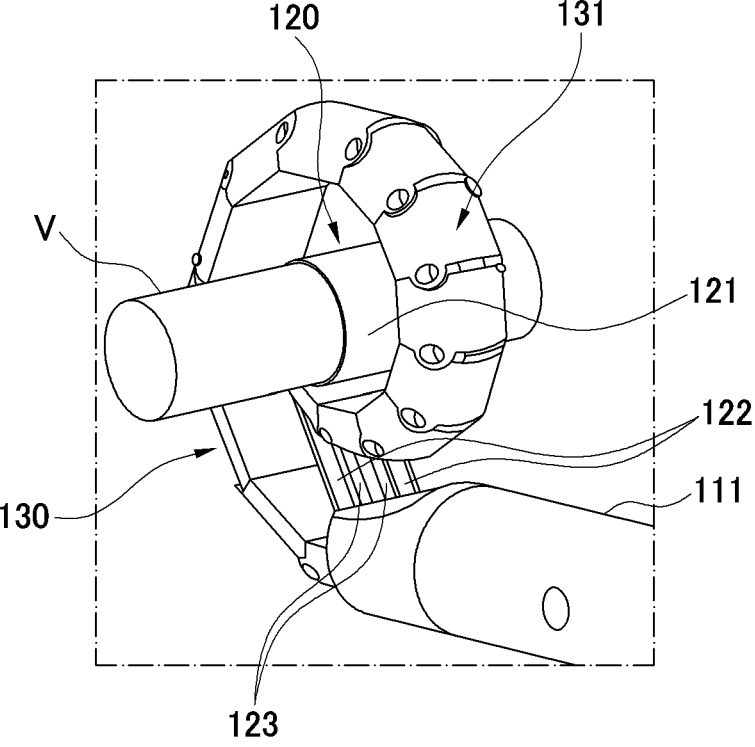
FIG. 2 is a perspective view illustrating a wound state of an electrode guide according to an embodiment of the present disclosure.
Figure 3A:
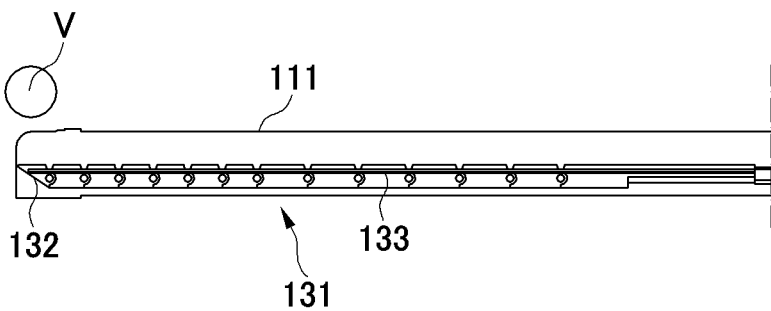
FIG. 3A illustrates a process of deforming the electrode guide into a wound state according to an embodiment of the present disclosure.
Figure 3B:
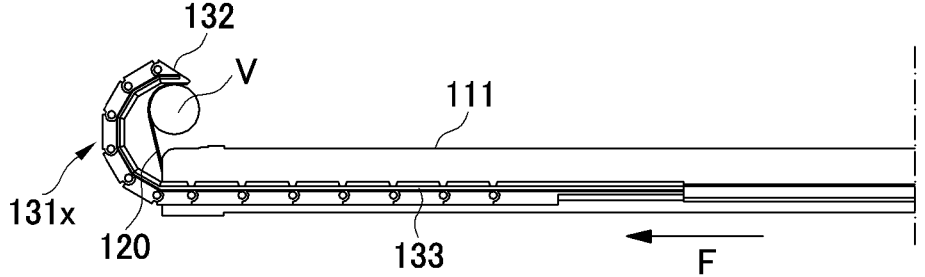
FIG. 3B illustrates a process of deforming the electrode guide into a wound state according to an embodiment of the present disclosure.
Figure 3C:
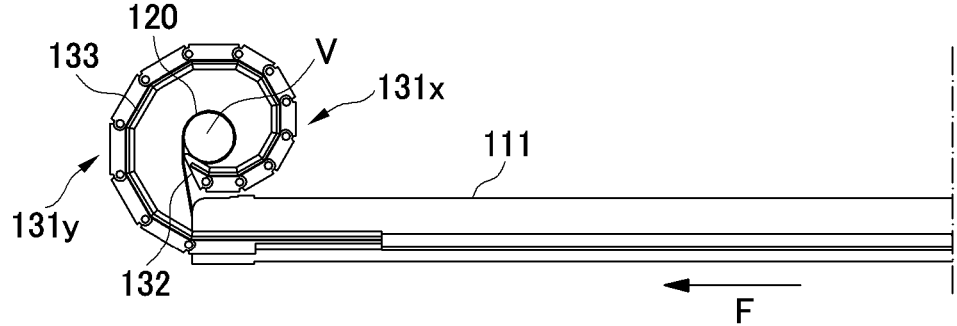
FIG. 3C illustrates a process of deforming the electrode guide into a wound state according to an embodiment of the present disclosure.
Figure 4:
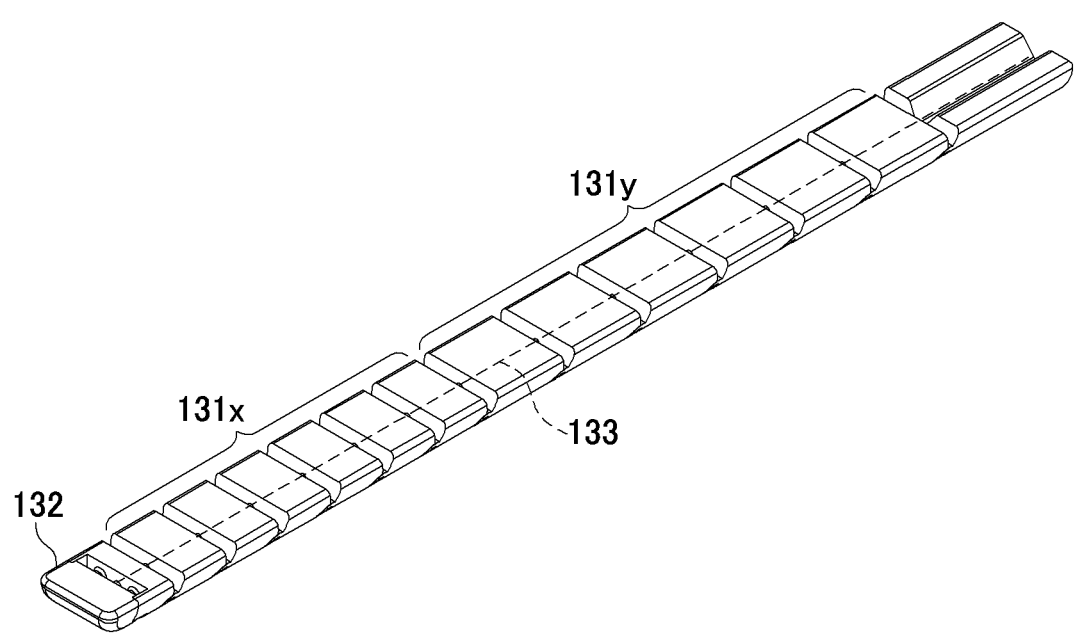
FIG. 4 is a perspective view illustrating a body portion and a coupling portion of the electrode guide according to an embodiment of the present disclosure.

FIG. 1 is a side view of an electrode device 100 according to an embodiment of the present disclosure. FIG. 2 is a perspective view illustrating a wound state of an electrode guide 130 according to an embodiment of the present disclosure. FIG. 3A through FIG. 3C illustrate a process of deforming the electrode guide 130 into a wound state according to an embodiment of the present disclosure. FIG. 4 is a perspective view illustrating a body portion 131 and a coupling portion 132 of the electrode guide 130 according to an embodiment of the present disclosure.

Referring to FIG. 1, the electrode device 100 according to an embodiment of the present disclosure includes the main body 110, the electrode unit 120 and the electrode guide 130.

The main body 110 may include the shaft 111 extending in one direction, a grip portion 112 connected to the shaft 111 so as to be gripped by an operator, a guide manipulation unit 113 formed on the grip portion 112 so as to manipulate an operation of the electrode guide 130, and an electrode manipulation unit 114 formed on the grip portion 112 so as to manipulate energy transfer to the electrode unit 120. The components for driving and controlling the electrode unit 120 and the electrode guide 130 may be located inside the main body 110.

The electrode unit 120 and the electrode guide 130 are formed to be drawn out from one end of the shaft 111 and configured to denervate or modulate at least part of nerves distributed on a tissue in the body including a tube depending on manipulation by the operator.

For example, as illustrated in FIG. 2, the electrode unit 120 may be brought into contact with a tube-shaped tissue V in the body by enclosing an outer surface of the tissue V and may transmit electrical impulses or various energies to the nerves distributed on the tissue V to denervate or modulate at least some of the nerves.

Here, the electrode guide 130 may perform a function of bringing the electrode unit 120 into contact with the tubular tissue V. The electrode guide 130 may be coupled to the electrode unit 120 and deformed into a wound state to bring the electrode unit 120 into contact with the tube-shaped tissue V. For example, the state illustrated in FIG. 2 and FIG. 3C may be the wound state.

Referring to FIG. 3A through FIG. 3C and FIG. 4, the electrode guide 130 of the present disclosure may include the body portion 131 and the coupling portion 132 in order to be deformed into the wound state. In the wound state, the body portion 131 is disposed to enclose the circumference of the tube-shaped tissue V with the electrode unit 120 interposed therein.

According to an embodiment of the present disclosure, the electrode guide 130 is accommodated together with the electrode unit 120 inside the shaft 111 and may protrude from one end in a forward direction F while being deformed into the wound state at the time of surgical procedure.

As illustrated in FIG. 3A through FIG. 3C, when the plurality of joint units 131 is sequentially drawn out, the plurality of joint units 131 may move toward one direction and thus may overall enclose the tube V in the wound state. In the wound state, the electrode guide 130 is spaced apart from an outer circumferential surface of the tube and the electrode unit 120 located inside the wound electrode guide 130 may be in close contact with the outer circumferential surface of the tube V.

According to an embodiment of the present disclosure, the body portion 131 may include a first body group 131x and a second body group 131y. As illustrated in FIG. 3A through FIG. 4, the first body group 131x may have a first length in a longitudinal direction, and the second body group 131y may have a second length greater than the first length. For example, each of the first body group 131x and the second body group 131y may include, for example, six joints respectively having different lengths.

Due to such a difference in length between the first body group 131x and the second body group 131y, the first body group 131x may form a first radius of curvature and the second body group 131y may form a second radius of curvature greater than the first radius of curvature in the wound state. That is, as can be seen from FIG. 3C, the joints having a relatively small length (the first body group 131x) may form a smaller radius of curvature and the joints having a relatively great length (the second body group 131y) may form a greater radius of curvature.

Specifically, the first body group 131x forming the first radius of curvature may be located close to the coupling portion 132, and the second body group 131y forming the second radius of curvature may be located close to the shaft 111.

When the body portion 131 located close to the coupling portion 132 forms a smaller radius of curvature in the wound state, a path along which the coupling portion 132 enters a space between the tube-shaped tissue V and the shaft 111 may be formed as shown in FIG. 3C. The electrode guide 130 including the body portion 131 may have an overall spiral shape.

Figure 5:
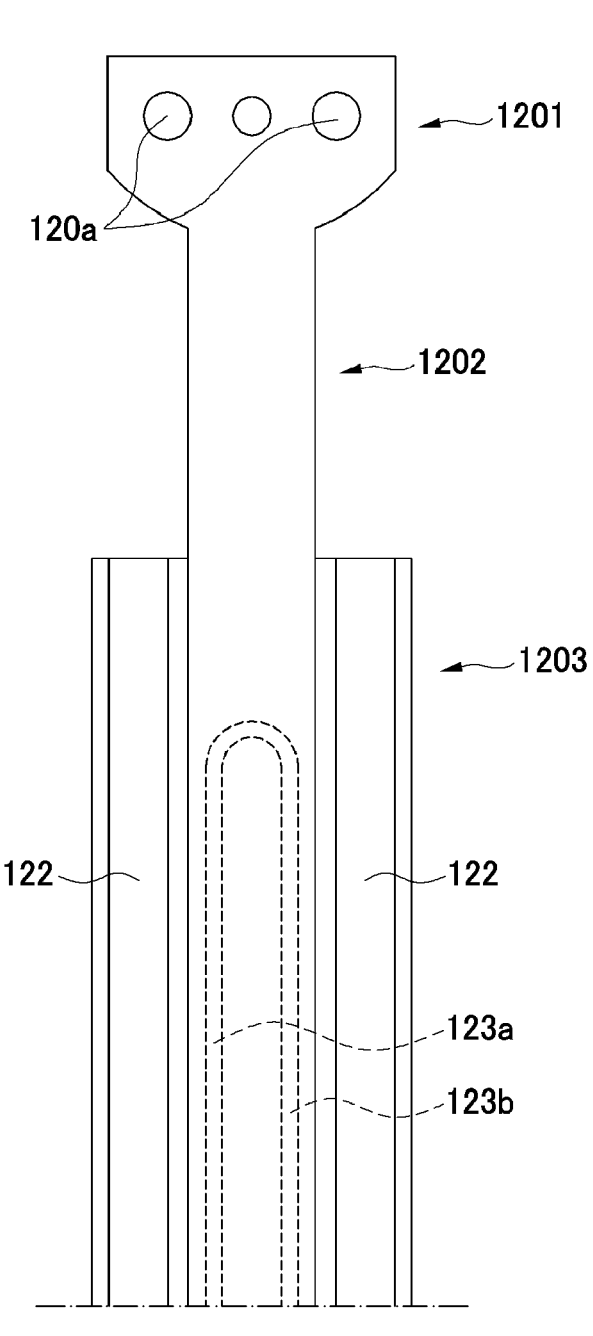
FIG. 5 is a plan view illustrating a portion of an electrode unit according to an embodiment of the present disclosure.
Figure 6A:
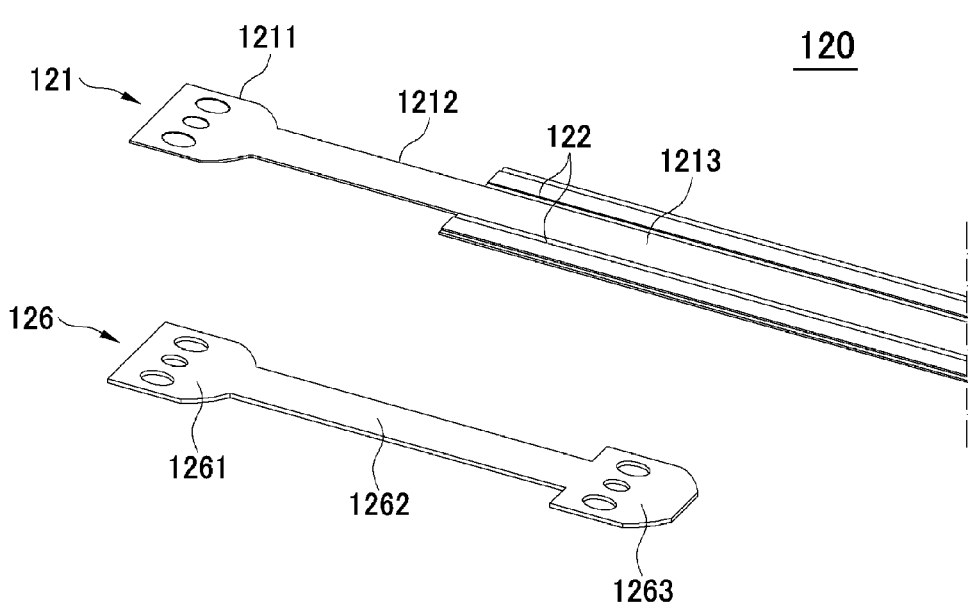
FIG. 6A is an exploded perspective view of an electrode unit according to an embodiment of the present disclosure.
Figure 6B:
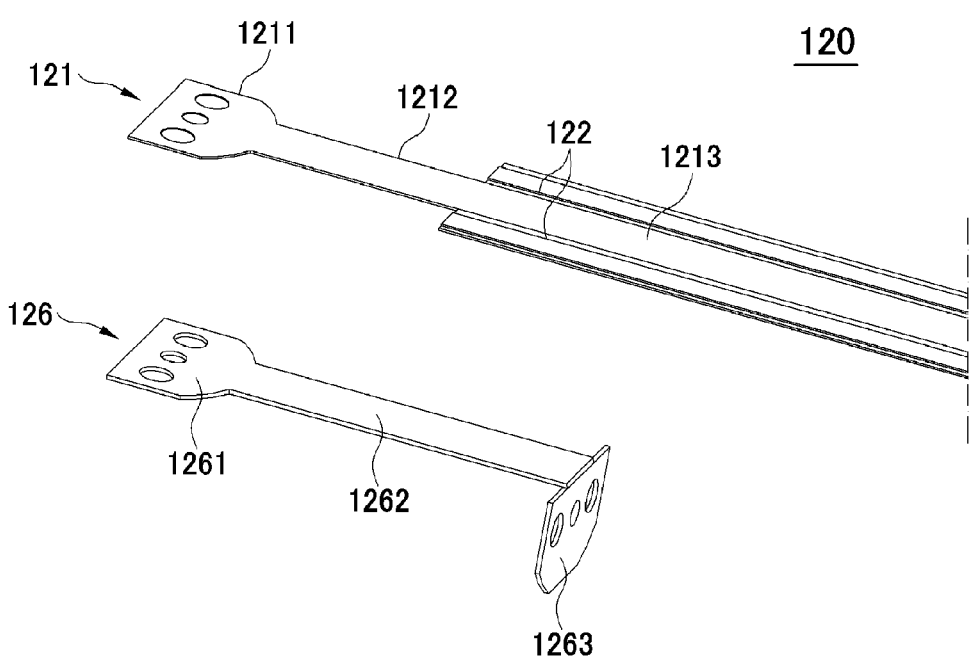
FIG. 6B is an exploded perspective view of an electrode unit according to an embodiment of the present disclosure.
Figure 7:
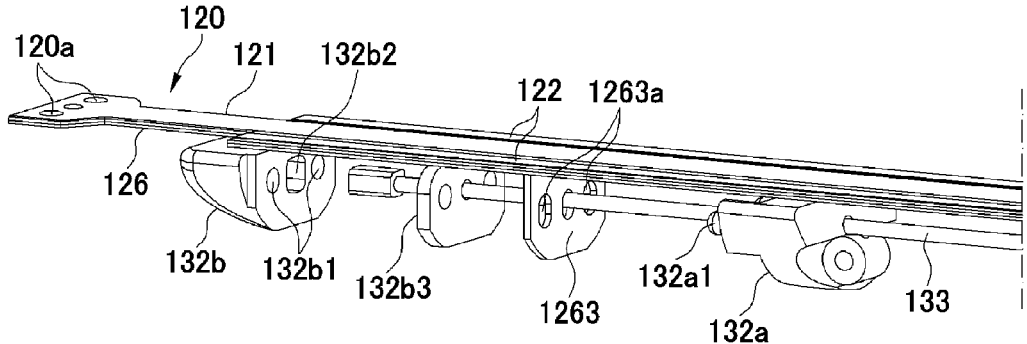
FIG. 7 is an exploded perspective view of the electrode unit and the coupling portion according to an embodiment of the present disclosure.
Figure 8:
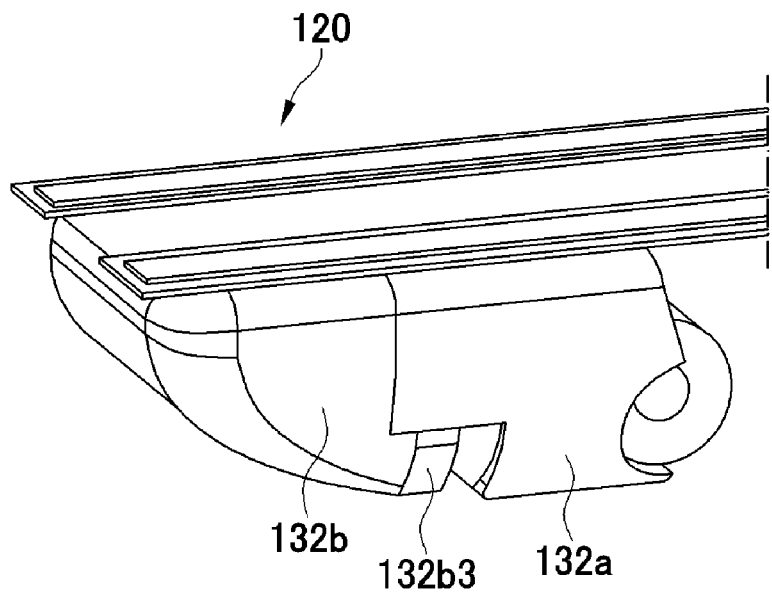
FIG. 8 is a perspective view illustrating a state where the electrode unit and the coupling portion are coupled to each other according to an embodiment of the present disclosure.

FIG. 5 is a plan view illustrating a portion of an electrode unit according to an embodiment of the present disclosure. FIG. 6A through FIG. 6B are an exploded perspective view of an electrode unit according to an embodiment of the present disclosure. FIG. 7 is an exploded perspective view of the electrode unit and the coupling portion according to an embodiment of the present disclosure. FIG. 8 is a perspective view illustrating a state where the electrode unit and the coupling portion are coupled to each other according to an embodiment of the present disclosure.

The electrode unit 120 according to an embodiment of the present disclosure may be provided in an electrode device for nerve denervation or modulation in vivo and disposed to enclose a tube-shaped tissue in the body. As illustrated in FIG. 5, the electrode unit 120 may be formed by sequentially extending a fastening portion 1201, an extension portion 1202 and an electrode portion 1203.

The fastening portion 1201 may have a through-hole 120a so as to be coupled to the coupling portion 132 which will be described with reference to FIG. 7 and FIG. 8.

When the electrode unit 120 encloses a tube-shaped tissue in the body, the electrode portion 1203 may be brought into contact with an outer surface of the tube-shaped tissue and may enclose the tube-shaped tissue. In order for the electrode portion 1203 to enclose the outer surface of the tube-shaped tissue and transfer energy thereto, the electrode unit 120 may be configured as a flexible printed circuit board (PCB) for transferring RF energy, a transducer for transferring ultrasonic energy or a metal electrode for transferring high-voltage energy.

An electrode 122 capable of transferring energy to the tube-shaped tissue may be formed on the electrode portion 1203 of the electrode unit 120. The electrode 122 may be composed of two bipolar electrodes extending parallel to each other on the electrode portion 1203.

The electrode 122 may be made of a material such as stainless steel or gold, which is harmless to the human body and conducts electricity well, in order to block or denervate or control or modulate the nerves. Also, the electrode 122 may transfer various types of energy from an energy source generator.

For example, the energy may include radio-frequency (RF) energy, electrical energy, laser energy, ultrasonic energy, high-intensity focused ultrasound energy, cryogenic energy and other heat energy.

Also, a sensor unit 123 may be disposed between the electrodes 122 on the electrode portion 1203, and the sensor unit 123 may be a thermocouple composed of a first metal 123a and a second metal 123b. For example, the sensor unit 123 may be formed a pair of copper and constantan. When neurotomy is performed with the electrode device 100 according to an embodiment of the present disclosure, the sensor unit 123 may monitor a temperature of a treatment site or may measure signals from the nerves on the tissue V.

Further, the electrode unit 120 according to an embodiment of the present disclosure may include an electrode layer 121 and a fixing layer 126 stacked with the electrode layer 121 as illustrated in FIG. 6.

The electrode layer 121 may be formed by sequentially extending an electrode layer fastening portion 1211, an electrode layer extension portion 1212 and an electrode layer electrode portion 1213.

Also, the fixing layer 126 may be stacked with the fastening portion 1211, the extension portion 1212 and a part of the electrode portion 1213 of the electrode layer 121.

The fixing layer 126 is composed of a first fastening portion 1261 formed at one end, a second fastening portion 1263 formed at the other end and a connection portion 1262 connecting the first and second fastening portions 1261 and 1263.

The first fastening portion 1261 of the fixing layer may correspond to the electrode layer fastening portion 1211 and may be stacked with the electrode layer fastening portion 1211 to form the fastening portion 1201 of the electrode unit.

The connection portion 1262 of the fixing layer may extend to the extension portion 1212 and a part of the electrode portion 1213 of the electrode layer 121. Here, a part of the connection portion 1262 of the fixing layer may correspond to the extension portion 1212 of the electrode layer and may be stacked with the extension portion 1212 of the electrode layer to form the extension portion 1202 of the electrode unit. Further, the other part of the connection portion 1262 of the fixing layer may be stacked with the electrode portion 1213 of the electrode layer.

A boundary between the connection portion 1262 and the second fastening portion 1263 of the fixing layer may be formed to bend the connection portion 1262 and the second fastening portion 1263 of the fixing layer as illustrated in FIG. 6B.

Hereafter, coupling of the electrode guide and the electrode unit 120 will be described with reference to FIG. 7 and FIG. 8.

In the electrode guide, the coupling portion 132 is connected to the end of the body portion 131 and configured to fix an end of the electrode unit 120. As illustrated in FIG. 7, the coupling portion 132 may include a first clamping piece 132a and a second clamping piece 132b. The electrode guide may further include a joint wire 133 which penetrates the body portion and is coupled to the second clamping piece 132b to guide the body portion to be in the wound state.

The joint wire 133 may be formed to sequentially penetrate the body portion. The joint wire 133 can guide the electrode guide to be deformed into a shape enclosing the tube in the body.

The second clamping piece 132b may include a wire groove 132b2 formed to allow insertion of an end of the joint wire 133 and a fixing plate 132b3 configured to close a portion of the wire groove in order to suppress deviation of an end of the joint wire 133 from the wire groove 132b2.

The wire groove 132b2 may be formed to accommodate an end of the joint wire 133 between a plurality of fastening grooves 132b1 provided in the second clamping piece 132b. The end of the joint wire 133 inserted into the wire groove 132b2 may have a greater diameter than the wire 133 or may have a different shape from the wire 133 and thus may be caught and fixed in the fixing plate 132b3 without deviation from the wire groove 132b2.

Further, the first clamping piece 132a may be fixed to the body portion, and the second clamping piece 132b may be coupled to the first clamping piece 132a with a portion of the electrode unit 120, desirably the fastening portion 1201 of the electrode unit and the second fastening portion 1263 of the fixing layer, interposed therebetween.

Hereafter, a coupling structure of the first clamping piece 132a and the second clamping piece 132b will be described. Any one of the first clamping piece 132a and the second clamping piece 132b according to an embodiment of the present disclosure may include a protrusion 132a1 protruding in one direction and the other one of the first clamping piece 132a and the second clamping piece 132b may include a fastening groove 132b1 recessed corresponding to the protrusion 132a1.

For example, if the protrusion 132a1 is provided in the first clamping piece 132a, the fastening groove 132b1 may be provided in the second clamping piece 132b, or if the protrusion is provided in the second clamping piece 132b, the fastening groove may be provided in the second clamping piece 132b.

The protrusion 132a1 provided in the first clamping piece 132a may penetrate the second fastening portion of the fixing layer and the fastening portion of the electrode unit 120 and may be coupled to the fastening groove 132b1 provided in the second clamping piece 132b. Here, throughholes 120a and 1263a through which the protrusion 132a1 penetrates may be formed in the fastening portion 1201 of the electrode unit and the second fastening portion 1263 of the fixing layer, respectively.

If the first clamping piece 132a and the second clamping piece 132b are coupled to each other in a state where the fastening portion 1201 of the electrode unit and the second fastening portion 1263 of the fixing layer are interposed between the first clamping piece 132a and the second clamping piece 132b, the electrode unit 120 may be stably fixed to the second clamping piece 132b while enclosing the second clamping piece 132b as illustrated in FIG. 8. Specifically, the fastening portion, the extension portion and a part of the electrode portion of the electrode layer and the fixing layer may enclose the second clamping piece 132b.

Figure 9A:
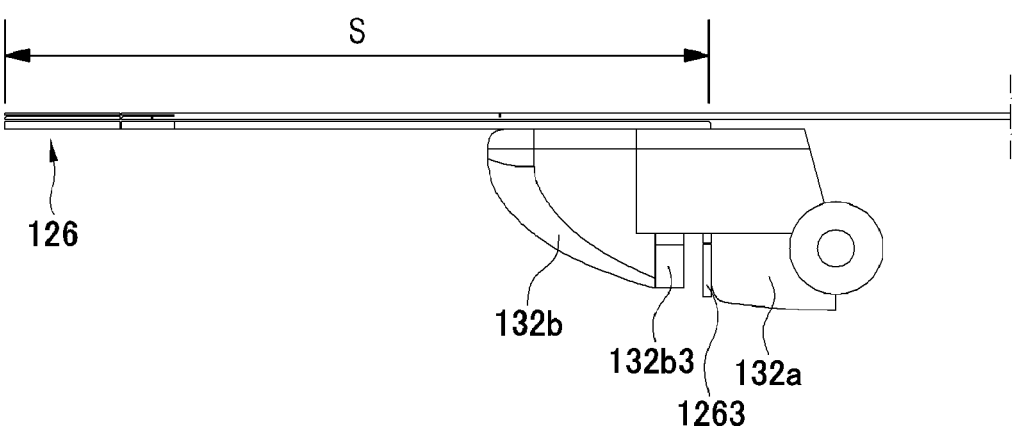
FIG. 9A is a side view illustrating an attachment state between an electrode layer and a fixing layer of the electrode unit according to an embodiment of the present disclosure.
Figure 9B:
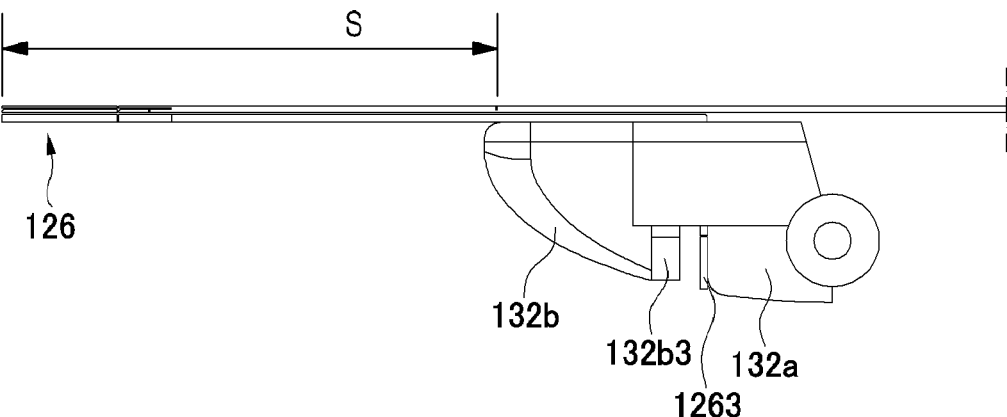
FIG. 9B is a side view illustrating an attachment state between an electrode layer and a fixing layer of the electrode unit according to an embodiment of the present disclosure.
Figure 10A:
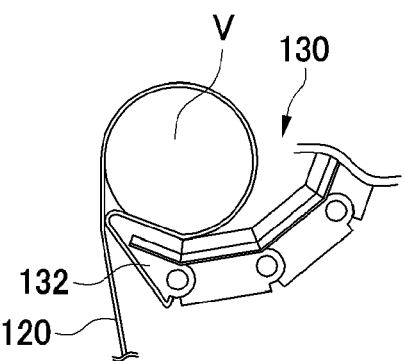
FIG. 10A illustrates a state where the electrode guide and the electrode unit enclose a tube-shaped tissue in the attachment state illustrated in FIG. 9A.
Figure 10B:
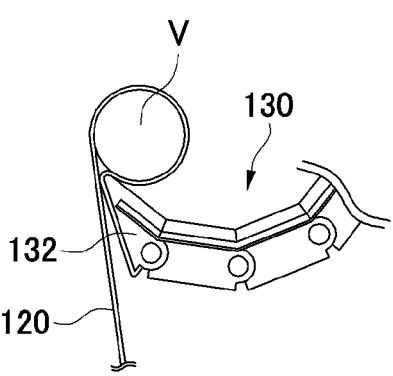
FIG. 10B illustrates a state where the electrode guide and the electrode unit enclose a tube-shaped tissue in the attachment state illustrated in FIG. 9B.

FIG. 9A and FIG. 9B are side views illustrating attachment states between the electrode layer 121 and the fixing layer 126 of the electrode unit according to an embodiment of the present disclosure, and FIG. 10A and FIG. 10B illustrate states where the electrode guide 130 and the electrode unit 120 enclose the tube-shaped tissue V in the attachment states illustrated in FIG. 9A and FIG. 9B, respectively.

In FIG. 9, a tip end (a left end) of the coupling portion 132 accords with a boundary between the extension portion and the electrode portion of the electrode unit. It can be seen from FIG. 9A that an area S corresponds to the fastening portion, the extension portion and a part of the electrode portion of the electrode unit and the first fastening portion and the connection portion of the fixing layer. Also, it can be seen from FIG. 9B that the area S corresponds to the fastening portion and the extension portion of the electrode unit and the first fastening portion and the connection portion of the fixing layer.

The fixing layer 126 according to an embodiment of the present disclosure may be attached to the electrode layer 121 while being stacked with the electrode layer 121.

For example, in the area S illustrated in FIG. 9A, the fixing layer 126 may be attached to the electrode layer 121. That is, all of the first fastening portion and the connection portion of the fixing layer 126 may be attached to the electrode layer 121. Thus, the first fastening portion of the fixing layer 126 may be attached corresponding to the fastening portion of the electrode layer 121, and all of the connection portion of the fixing layer 126 may be attached to the extension portion of the electrode layer 121 and a part of the electrode portion of the electrode layer 121.

In this attachment state, the electrode guide 130 and the electrode unit 120 may enclose the tube-shaped tissue V as illustrated in FIG. 10A. Here, the electrode guide 130 may be deformed into the wound state to bring the electrode unit 120 into contact with the tube-shaped tissue V and may be disposed to enclose the circumference of the tube-shaped tissue V with the electrode unit 120 interposed therein. The electrode unit 120 may enclose the tissue V while being in contact with the outer surface of the tissue V in a state where a part of the electrode portion is in contact with the second clamping piece, which is the first joint of the coupling portion 132.

Otherwise, the fixing layer 126 may be attached to the electrode layer 121, but may not be attached to at least a part of the electrode portion of the electrode layer 121.

For example, in the area S illustrated in FIG. 9B, the fixing layer 126 may be attached to the electrode layer 121. That is, the first fastening portion and a part of the connection portion of the fixing layer 126 may be attached to the electrode layer 121. Thus, the first fastening portion of the fixing layer 126 may be attached corresponding to the fastening portion of the electrode layer 121, and a part of the connection portion of the fixing layer 126 may be attached to the entire extension portion of the electrode layer 121. Further, the other part of the connection portion of the fixing layer 126 may not be attached to the electrode layer 121, particularly the electrode portion of the electrode layer 121.

In this attachment state, the electrode guide 130 and the electrode unit 120 may enclose the tube-shaped tissue V as illustrated in FIG. 10B. Here, the electrode portion of the electrode unit 120 is not in contact with the second clamping piece, which is the first joint of the coupling portion 132, and, thus, the electrode unit can form a smaller radius of curvature. Therefore, the electrode unit can enclose the tube-shaped tissue V having a smaller diameter, as compared to the attachment state illustrated in FIG. 9A.

Alternatively, although not illustrated in the drawings, the first fastening portion of the fixing layer may be attached corresponding to the fastening portion of the electrode layer, a part of the connection portion of the fixing layer may be attached to the extension portion of the electrode layer and a part of the electrode portion of the electrode layer, and the other part of the connection portion of the fixing layer may not be attached to the electrode portion of the electrode layer.

The electrode unit in this attachment state may form a smaller radius of curvature than the electrode unit in the attachment state illustrated in FIG. 9A and a greater radius of curvature than the electrode unit in the attachment state illustrated in FIG. 9B.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described as a single type may be implemented in a dispersed form, and likewise components described as distributed may also be implemented in a combined form.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. An electrode unit provided in an electrode device for denervation or modulation of nerves in vivo and disposed to enclose a tube-shaped tissue in a body, comprising:
  an electrode layer formed by sequentially extending a fastening portion, an extension portion and an electrode portion, and the electrode portion including an electrode on one side and configured to enclose the tube-shaped tissue; and
  a fixing layer stacked with the fastening portion, the extension portion and a part of the electrode portion of the electrode layer,
  wherein the fixing layer includes:
  a first fastening portion formed on a first end of the fixing layer to correspond to the fastening portion;
  a second fastening portion formed on a second end of the fixing layer; and
  a connection portion connecting the first and second fastening portions, and
  a boundary between the connection portion and the second fastening portion is formed to be bendable.

2. The electrode unit of claim 1,
  wherein the fixing layer is attached to the electrode layer, but at least a part of the electrode portion of the electrode layer is not attached to the fixing layer.

3. The electrode unit of claim 1,
  wherein the first fastening portion of the fixing layer is attached corresponding to the fastening portion of the electrode layer, and all of the connection portion of the fixing layer is attached to the extension portion of the electrode layer and a part of the electrode portion of the electrode layer.

4. The electrode unit of claim 1,
  wherein the first fastening portion of the fixing layer is attached corresponding to the fastening portion of the electrode layer, and a part of the connection portion of the fixing layer is attached to the entire extension portion of the electrode layer, but the other part of the connection portion of the fixing layer is not attached to the electrode portion of the electrode layer.

5. The electrode unit of claim 1,
  wherein the first fastening portion of the fixing layer is attached corresponding to the fastening portion of the electrode layer, a part of the connection portion of the fixing layer is attached to the extension portion of the electrode layer and a part of the electrode portion of the electrode layer, and the other part of the connection portion of the fixing layer is not attached to the electrode portion of the electrode layer.

6. The electrode unit of claim 1, further comprising:

a sensor unit disposed on the electrode portion of the electrode layer and configured to detect a temperature.

7. An electrode device for denervation or modulation of nerves in vivo, comprising:

an electrode unit of disposed to enclose a tube-shaped tissue in a body; and an electrode guide deformed into a wound state to bring the electrode unit into contact with the tube-shaped tissue, wherein the electrode unit comprises:

an electrode layer formed by sequentially extending a fastening portion, an extension portion and an electrode portion, and the electrode portion including an electrode on one side and configured to enclose the tube-shaped tissue; and a fixing layer stacked with the fastening portion, the extension portion and a part of the electrode portion of the electrode layer, wherein the electrode guide includes:

a body portion which is spaced apart from the electrode unit to enclose the circumference of the tube in the wound state; and a coupling portion which is connected to the end of the body portion and to which a fastening portion of the electrode unit is fixed, and wherein the coupling portion includes:

a first clamping piece fixed to the body portion; and a second clamping piece coupled to the first clamping piece with the fastening portion of the electrode unit interposed therebetween.

8. The electrode device of claim 7, wherein any one of the first clamping piece and the second clamping piece includes a protrusion protruding in one direction, the other one of the first clamping piece and the second clamping piece includes a fastening groove recessed corresponding to the protrusion, and the fastening portion of the electrode unit includes a through-hole through which the protrusion penetrates.

9. The electrode device of claim 7, wherein the fastening portion of the electrode unit is inserted between the first clamping piece and the second clamping piece.

10. The electrode device of claim 7, wherein the electrode guide further includes a joint wire which penetrates the body portion and is coupled to the second clamping piece to guide the body portion to be in the wound state, and the second clamping piece includes:

a wire groove formed to allow insertion of an end of the joint wire; and a fixing plate configured to close a portion of the wire groove in order to suppress deviation of the end of the joint wire from the wire groove.

\* \* \* \* \*